United States Patent [19]

Bashkovich et al.

[11] 4,075,322
[45] Feb. 21, 1978

[54] ENZYME COMPOSITION

[76] Inventors: Alexandr Pavlovich Bashkovich, prospekt M. Toreza, 40, korpus 7, kv. 21; Evgenia Semenovna Zimnukhova, ulitsa Pionerstroya, 18, kv. 206; Agnessa Vladimirovna Prokopovich, Bolsheokhtinsky prospekt, 79, kv. 9; Olga Grigorievna Polatovskaya, ulitsa Uchitelskaya, 19, korpus 1, kv. 29; Maria Ivanovna Pronina, ulitsa Sedova, 109, kv. 33; Valter Osvaldovich Kulbakh, Bukharestskaya ulitsa, 86, korpus 1, kv. 85; Khasya Ionovna Rivkina-Pevtsova, ulitsa Sadovaya, 92, kv. 5; Grigory Efimovich Grinberg, prospekt Metallistov, 82, kv. 321, all of Leningrad, U.S.S.R.

[21] Appl. No.: 593,536

[22] Filed: July 7, 1975

Related U.S. Application Data

[63] Continuation of Ser. No. 418,847, Nov. 26, 1973, abandoned.

[51] Int. Cl.$^2$ .............................................. A61K 37/48
[52] U.S. Cl. ....................................... 424/94; 195/62; 424/114; 424/115
[58] Field of Search ................ 424/94, 114, 115, 123, 424/124; 195/62, 65

[56] References Cited

FOREIGN PATENT DOCUMENTS

| 7,646 | 2/1970 | France | 424/94 |
|---|---|---|---|
| 2,239,650 | 2/1973 | Germany | 424/94 |

OTHER PUBLICATIONS

Egorov, Chem. Abs., vol. 77, 1972, Ab. No. 123754w.
Egorov, Chem. Abs., vol. 76, 1972, Ab. No. 152026v.
Gauze, Chem. Abs., vol. 66, 1967, Ab. No. 93962r

*Primary Examiner*—Albert T. Meyers
*Assistant Examiner*—A. P. Fagelson
*Attorney, Agent, or Firm*—Holman & Stern

[57] ABSTRACT

An enzyme of hydrolytic action, according to the invention, is a neutral protease having the molecular weight of about 37,000, the isoelectric point at pH 8.8, the optimum activity at 40° – 45° C, the stability range in aqueous solutions at pH 6.8 – 8.0, quickly inactivating in said solutions at temperatures above 50° C.

The enzymatic preparation containing the enzyme of hydrolytic action in an amount of 50 – 500 PU/g and the metabolites of the strains *Streptomyces hygroscopicus*.

A method for preparing the hydrolytic enzyme, in which the strain *Streptomyces hygroscopicus* is cultivated on media containing assimilable sources of carbon and nitrogen, inorganic mineral salts, in deep aerobic conditions, with accumulation of the enzyme of hydrolytic action and the metabolites of the said strains in the culture fluid, followed by subsequent isolation of the enzyme.

A medicinal preparation for treating respiratory diseases, purulent wounds and thermal burns, for treating and preventing empyema of the pleura, containing the enzyme of hydrolytic action in the quantity of 1 – 50 PU/mg, inactive protein and mineral salts.

6 Claims, No Drawings

ENZYME COMPOSITION

This is a continuation of application Ser. No. 418,847 filed Nov. 26, 1973, now abandoned.

BACKGROUND AND SUMMARY OF THE INVENTION

This invention relates to a new enzyme of hydrolytic action and enzymatic preparations, and also to a method for preparing them and their uses.

The said enzyme of hydrolytic action is a neutral protease having the molecular weight of about 37,000, the isoelectric point at pH 8.8, the optimum activity at a temperature of 40° – 45° C, the stability range in aqueous solutions at pH 6.0 – 8.0, quickly inactivating in said solutions at temperatures above 50° C.

We gave this enzyme of hydrolytic action the name hygrolytin.

Hygrolytin is a white odourless powder readily soluble in water, in an isotonic sodium chloride solution, hypertonic sodium chloride solution, in 0.25 to 2.0% novocain solutions, insoluble in lower alcohols or acetone, absorbing in the UV region of the spectrum characteristic of proteins. Calcium ion stabilizes the enzymatic activity of hygrolytin. The action of magnesium ion is similar, but less pronounced. EDTA, and other compounds binding calcium ion, inactivate the enzymatic activity of hygrolytin.

Hygrolytin can form salts with soluble and cross-linked poly-electrolytes having carboxy groups, and also can be sorbed on some polymers and sorbents.

The structure of hygrolytin has not yet been established.

The specific caseinolytic activity of hygrolytin exceeds by two or three times that of the known enzymes of the animal origin, trypsin and α-chemotrypsin.

The enzyme hygrolytin has the power of hydrolysing native proteins, such as elastin, collagen, gelatin, fibrin, albumin, hemoglobin, and also displays its power of thrombolysis and of preventing thrombs, as well as milk-coagulating activity.

The said enzyme can be used in various branches of economy where hydrolysis of proteinous substrates is required, for example, in agriculture for hydrolysis of protein components of animal feeds to improve their assimilability, in food industry (in baking, brewing, meat softening), in microbiological industry for hydrolysis of protein components (for example, yeast) in the preparation of nutrient media, in photography for extraction of gelatin-bound silver from wastes, in leather industry for scouring and softening raw hide.

Hygrolytin possesses proteolytic activity and hence can be used to thin viscous, thick suppurative exudates during treatment of diseases of the respiratory organs, purulent and thermal burn wounds, for treating and preventing empyema of the pleura.

Hygrolytin can also be used as a thrombolytic preparation and as a remedy preventing the formation of thrombs, as well as in combination with anticoagulants.

The use of the enzyme offers good economy owing to the low cost of the product itself when produced alongside with antibiotic hygromycin B.

The enzymatic preparation, which is an impure (crude) product, contains the enzyme of hydrolytic action in the quantity of 50 – 500 PU/g (proteolytic units after Kunitz) and the metabolites of the strain *Streptomyces hygroscopicus* producing the enzyme.

The said enzymatic preparation is a brown powder.

DESCRIPTION OF THE PREFERRED EMBODIMENTS

The method for preparing the enzyme of hydrolytic action, according to the invention, consists in that the strains *Streptomyces hygroscopicus*, producing the enzyme, are cultivated on media containing assimilable sources of carbon and nitrogen, mineral salts, in deep aerobic condition, with accumulation of the enzyme hygrolytin in the culture fluid (together with the metabolites of the said strains), and final isolation of the enzyme. The formation of two and more proteases which compose the active enzyme hygrolytin is possible.

The medium used for the fermentation has the following composition (in percent by weight): soya bean flour 1 – 1.5%, corn steep liquor 0.2 – 0.3%, sperm oil 1 – 2.5%, glucose 0.8 – 1.5%, ammonium sulphate 0.2 – 0.8%, sodium chloride to 0.5%, calcium carbonate 0.3 – 0.8%, and dry yeast (protein-vitamin complex) 0.8 – 1.6%.

It is desirable to isolate the main product by separating the culture fluid from the propagated strains (the biomass) producing the enzyme hygrolytin, with subsequent precipitation of the enzyme from the filtrate by ammonium sulphate taken in an amount of 50 – 60 percent of the filtrate volume, and subsequent re-precipitation of the obtained precipitate from acetone, with dissolution of the obtained precipitate in calcium chloride solution, depigmentation of the solution with activated carbon, sterilization and lyophilic drying of the said solution to prepare the medicinal preparation.

In order to obtain pure enzyme of hydrolytic action, the lyophilized powder is dissolved in a 0.001 M solution of calcium chloride, the prepared solution is passed through columns packed with gel sorbents, and lyophilized.

The main product can be isolated by concentrating the culture fluid with subsequent drying of the thus-obtained enzymatic preparation.

The main product can be isolated also by separating the propagated strains (the biomass) from the culture fluid with subsequent concentration of the filtrate and drying.

The enzyme can be prepared by cultivting strain No. 1913, deposited in the collection of cultures producing antibiotics at the All-Union Research Institute for Antibiotics, Moscow (deposit No. 997), *Streptomyces hygroscopicus* (Jensen 1931), that produces also antibiotic hygromycin B which accumulates in the culture liquid and is isolated from the culture fluid by cation-exchange process prior to isolating the final product.

Before isolating the antibiotic hygromycin B, the propagated strains No. 1913 *Streptomyces hygroscopicus* can be separated from the culture fluid.

Strain No. 1913 *Streptomyces hygroscopicus* (Jensen 1931) is grown on a synthetic czapek medium with starch:

| | |
|---|---|
| $K_2HPO_4$ | 1 g |
| $NaNO_3$ | 3 g |
| KCl | 0.5 g |
| $MgSO_4$ | 0.5 g |
| $FeSO_4$ | 0.015 g |
| Starch | 20 g |
| Agar-agar | 25 g |
| water | 1 liter |

The medium is sterilized for 30 minutes at 0.8 atm.

The pH after sterilization 7.0 – 7.1.

The strain forms compact spiral sporangiophores with 1 – 3 coils. The spores have the shapes of segments with wart-like formations. Aerial mycelium is well developed on both synthetic and organic media. The mycelium is not fragmented, sclerotia are absent. The colour of the aerial sporulating mycelium on czapek mineral medium with glucose is from greyish white to grey.

On Krasilnikov's synthetic medium having the composition:

| | |
|---|---|
| $KH_2PO_4$ | 3 g |
| $MgCO_3$ | 0,3 g |
| NaCl | 0,2 g |
| $KNO_3$ | 1.0 g |
| $FeSO_4$ | 0,001 g |
| $CaCO_3$ | 0.5 g |
| saccharose | 20 g |
| agar-agar | 15 g |
| water | 1 liter | sterilized at 110° C for 20 minutes and having the pH 7.0, the strain develops well, forming convex colonies 4 – 6 mm in diameter. The aerial mycelium is weakly sporulating, greyish-white in colour. The substrate mycelium is yellowish brown.

On czapek medium with starch, the colonies are 4 – 6 mm in dia, white, flat, asporogenic; the substrate mycelium is of pale sand colour.

On a starch-ammonia medium having the compositions:

| | |
|---|---|
| starch (soluble) | 10 g |
| $K_2HPO_4$ (anhydrous) | 1 g |
| $MgSO_4 \cdot 7H_2O$ | 1 g |
| NaCl | 1 g |
| $(NH_4)_2SO_4$ | 2 g |
| $CaCO_3$ | 2 g |
| water | 1 liter |
| agar-agar | 20 g | sterilized at 0.5 atm for thirty minutes, and having the pH 7.0 – 7.2, the colonies are large, flat, with aerial mycelium developed by the edge of the colony, from greyish-white to dark grey in colour. The substrate mycelium is colourless.

On organic medium No. 2 (Hause's)

| | |
|---|---|
| Hottinger digest | 21 mg % of amine nitrogen |
| peptone | 0.5 % |
| NaCl | 0.5 % |
| glucose | 1 % |
| agar-agar | 2.2 % | sterilized for thirty min at 0.5 atm and having the pH 7.2, the colonies are small, convex, with flour-like white mycelium; the substrate mycelium is brownish yellow.

On medium No. 21/12, with starch and corn steep liquor having the following composition:

| | |
|---|---|
| corn steep liquor | 5 g |
| $(NH_4)_2HPO_4$ | 4 g |
| $KH_2PO_4$ | 2 g |
| $MgSO_4$ | 0,25 g |
| $CaCO_3$ | 1 g |
| starch | 20 g |
| agar-agar | 20 g |
| water | 1 liter | sterilized for thirty minutes at 0.8 atm, and having the pH 7.0 – 7.2, the growth is intense, the aerial mycelium is from white to dark-smoke in colour.

On potato slices the growth is intense, without formation of spores, the aerial mycelium is white.

On Pridnam-Gottlieb medium with glucose, ramnose, d-fructose, d-mannitol, d-xylose, and raffinose, strain No. 1913 develops well, and only slightly develops on the medium having the same composition plus l-arabinose. The strain does not grow on a medium with saccharose and l-inositol.

On Van-Iterson medium having the composition:

| | |
|---|---|
| $NH_4NO_3$ | 0.05 g |
| $KH_2PO_4$ | 0.05 g |
| water | 100 ml |
| filter paper | | sterilized at 0.5 atm for thirty minutes, and containing cellulose, the growth of the strain is moderate, the gelatin completely softens, the nitrates are reduced, the milk peptonized, saccharose remains non-inverted, hydrogen sulphide is not formed, and starch is hydrolyzed intensely. At 50° C, and in the absence of oxygen, the strain does not grow.

The average antibiotic activity with respect to hygromycin B of strain No. 1913, under laboratory conditions on the above medium, is 2600 ± 200 units per ml. The proteolytic activity equals 37 ± 8 PU/ml.

As it has been stated above, the enzyme of hydrolytic action possesses proteolytic activity and is the active principle of a medicinal preparation intended for treating diseases of the respiratory organs, purulent wounds and thermal burns, for treatment and prophylaxis of empyema of the pleura, containing the said enzyme in the quantity of from 1 to 50 PU/mg, and inactive protein with mineral salts as a ballast material.

The medicinal preparation can be used externally in the powder form for local use.

When given for inhalation, or for endotracheal, endobroncheal or intrapleural administration, and also for local applications, the medicinal preparation contains the active principle in combination with a pharmaceutical solvent, which is sterile water, isotonic solution of sodium chloride, hypertonic solution of sodium chloride or a 0.25 – 2 percent aqueous solution of novocain.

The enzyme hygrolytin is contained in the said solvents in concentrations from 5 to 50 PU per ml.

When used in the powder form for external local applications, the medicinal preparation containing hygrolytin in combination with a filler material (starch) is used in the concentration of up to 500 PU per gram of the filler material.

The toxic and tolerated doses of the preparation containing hydrolytin were established in experiments in vivo. $LD_{50}$ for albino mice was 260 – 300 PU/kg body weight (when given intravenously). The experiments have also shown that the concentrations from 50 to 100 PU/ml are harmless when inhaled by rats, and also in local external applications in rabbits. The local action of the preparation containing hygrolytin on the crust of a thermal burn wound was tested on rabbits and rats. The preparation was applied externally in the powder form and then the wound was bandaged with sodium chloride solution. The preparation was also tested in the form of a wet bandage with a solution of the preparation in a 0.25 percent solution of novocain, and by introducing the preparation in the form of injections in the region of the crust. The doses of the preparation in the first two methods of administration were 50 – 100 PU, and for injections 5 – 10 PU/ml.

The reaction to the administration of the preparation by the three methods was delamination of the crust and its separation from the skin.

The power of hygrolytin to resolve necrotic tissues was studied in vitro on non-vital necrotized lung tissue taken from human patients during operations. It was established that hygrolytin vigorously hydrolyses non-vital tissues while intact tissues remain unaffected.

The experiments in vitro have also shown that the preparation containing hygrolytin can thin viscous sputum taken from patients.

The clinical study of the preparation containing hygrolytin was carried out on 267 patients. The preparation was given as aerosols for inhalations to patients with the diseases of the respiratory organs. The preparation was used in the liquid form containing 25 PU/ml of water, or isotonic solution of sodium chloride, the single dose being 75 – 125 PU.

The inhalation was given to patients once or twice a day in the course from five to seven days. For encotracheal administration, the preparation was used in the form of solution containing 8 – 10 PU/ml of isotonic solution of sodium chloride, in the volume not exceeding 5 ml, which was administered into the trachea through a catheter.

With the aim of preventing empyema of the pleura after pneumectomy, a solution of the preparation containing 250 PU in 50 ml of sterile solvent was administered into the pleural cavity at the end of the operation, after which the cavity was sutured without any fistulae. In the post-operative period the extudate was removed from the cavity by punctures (5 – 7 punctures) with administration of 250 PU of the preparation containing hygrolytin in 50 ml of sterile solvent in combination with an appropriate antibiotic.

For local administration, use was made of a solution of the preparation containing hygroyltin (25 – 50 PU/ml) in water, isotonic solution of sodium chloride, hypertonic solution of sodium chloride, or in aqueous solution of novocain.

The solution was used to soak a napkin which was then applied to the wound, and a water-proof bandage was placed on top. The bandage was renewed daily alongside with the removal of separated necrotic tissues.

In treating wounds, trophic ulcers and bedsores with extensive necrosis, and also burns of the third degree, the preparation containing hygrolytin was used in the form of powder in combination with starch (external application), containing up to 500 PU per gram of the filler. A sterile napkin slightly soaked in an isotonic solution of sodium chloride, or a 0.25 percent aqueous solution of novocain was placed over the powder, and finally a water-proof bandage was placed. The bandage was renewed once a day.

The clinical studies have shown that the preparation containing hygrolytin effectively thins viscous sputum, necrotic masses, and facilitates evacuation of mucus and purulent-necrotic masses. As a result, the function of the ciliated epithelium and mucous glands of the respiratory duct is restored, and the ventilation of the lungs is improved.

The pronounced thrombolytic activity of the preparation, and also its power to prevent thrombosis, has enabled us to use it effectively for prophylaxis of empyema of the pleura.

When used locally, the preparation containing hygrolytin showed its potency in treating purulent wounds and thermal burns, facilitating their freeing from pus, necronic tissues and fibrous formation, promotes delaminating and splitting of the crust, which facilitates granulation and improves the conditions for healing.

Thus, the preparation containing hygrolytin can be indicated for use in tracheitis, bronchitis, bronchotracheitis, pneumonia, bronchoectatic disease, abscesses of the lungs and other diseases of the respiratory organs associated with accumulation of viscous exudate, for treating and preventing empyema of the pleura, and also the local use in purulent wounds, bedsores, trophic ulcers, burns of the third degree, and in stomatology.

The side effect that may arise during the intake of the preparation is the tickling sensation in the throat, the cough reflex, possibly local pain and allergic reaction.

The contraindications for the use of the preparation containing hygrolytin are individual intolerance of the preparation, cardiovascular insufficiency of the II$a$, II$b$ and III degrees at the stage of decomposition, grave cavernous forms of pulmonary tuberculosis complicated by amyloidosis, cachexy, haemoptysis, susceptibility to haemorrhage, bleeding wounds and ulcers, and also ulceration of malignant tumours.

To patients with respiratory insufficiency of the III degree and broncheal asthma, as well as with wounds in which the main vessel is located, the preparation should be prescribed with precautions.

The preparation in the powder form can be stored in sterile vials in places protected from light at a temperature of 4° C during a period of one year.

The enzymatic preparation which is an impure (crude) product can be used in leather industry to scour and soften raw hides, in agriculture it can be used for hydrolysis of proteinous components of fodder to improve its assimilability, and for other purposes wherever hydrolysis of proteinous substrates may be required.

We gave this enzymatic preparation the name protohydrolytin.

The scouring and softening processes in leather industry effected with the aid of protohygrolytin substantially improve the efficiency of the process and its hygiene (improved quality and increased yields of hair, abolished alkaline ashing process).

The specificity of protohygrolytin action consists in that alongside with dissolution of cell structures and mucopolysaccharides which hold hair, the preparation promotes significantly the hydration of raw materials. This latter fact makes it possible to carry out the subequent steps of the process on the existing equipment (dehairing and bristling machines) without their special reconstruction, since the swollen raw materials pretreated with protohygrolytin solution possess sufficient resilience. The hydration of raw materials loosens the tissues due to the presence of moisture which penetrates the derma during skin processing. As a result, conditions are created to rule out the ashing process, since alongside with the hydration, the fermentation hydrolysis of interfibrillar proteins also takes place, the absence of the said proteins being usually associated with the necessity of carrying out the ashing process.

The method of processing all types of leather materials with protohygrolytin, during its trial under industrial conditions, has shown the applicability of the existing equipment for preparing leather and wool of proper quality.

The consumption of protohygrolytin having the activity of 80 PU/g was 1 – 7 percent of the weight of raw material, when the preparation was used in the bath and applied externally, the process continuing for 6 – 24 hours.

The method for preparing the enzyme of hygrolytic action, and the enzymatic preparation as well as the medicinal preparation should preferably be carried out as this.

Sterile nutrient medium containing 1.5 percent of soya bean flour, 1.5 – 2 percent of sperm oil, 0.2 percent of corn steep liquor, 0.8 – 1.2 percent of yeast (protein-vitamin complex), 0.2 percent of ammonium sulphate, 0.5 percent of sodium chloride, 0.3 percent of calcium carbonate, and 1.0 – 1.5 percent of glucose (percent by weight) is loaded into a fermentation tank. The culture medium is inoculated with strain No. 1913 *Streptomyces hygroscopicus* prepared by growing on a medium of the following composition (in percent by weight): 1 percent of soya bean flour, 0.2 percent of corn steep liquor, 1 percent of sperm oil, 1 percent of yeast, 0.2 percent of ammonium sulphate, 0.5 percent of sodium chloride, 0.3 percent of calcium carbonate and 1 percent of glucose, at a temperature of 28° C for 54 hours.

The fermentation process is carried out under pressure of 0.3 atm with aeration intensity of one volume of air per volume of the medium per minute at a temperature of 28° C for 168 – 192 hours.

On the termination of the fermentation process, the culture field is transferred into a receiving tank, processed with a solution of sodium oxalate to precipitate calcium ion at pH close to neutral, the biomass is separated and the precapitate of calcium salts is separated from the culture fluid. The culture fluid is passed through a battery of ion-exchange columns packed with carboxyl cation-exchange resins to remove the antibiotic hygromycin B.

The culture filtrate passed through the ion-exchangers and containing 10 – 50 units/ml of the antibiotic hygromycin B is collected in an apparatus and the enzyme hygrolytin is precipitated by ammonium sulphate added in the quantity of 50 – 60 percent of the solution volume under stirring. The mixture is allowed to stand in the cold for 6 – 10 hours to salt out, the salted out precipitate is separated by centrifuging and dissolved in 0.001M solution of calcium chloride. Then, an equal volume of cool acetone is added to the prepared solution in the cold, kept for thirty minutes and centrifuged again. The new precipitate is dissolved in 30 percent acetone, and the insoluble residue is separated on a centrifuge and discarded. Ten volumes of cool acetone are added to the separated supernatant liquid in the cold and the precipitate is separated, washed with cold acetone two times and dried in vacuo. The dry precipitate is then dissolved in a 0.001M solution of calcium chloride, activated charcoal is added, the mixture is stirred for 90 minutes and passed through a filter. The solution is then passed through a sterilizing filter, filled into vials and dried by lyophilization.

The solution can be depigmented also with ion-exchange resin, for example, anion-exchange resin, having the swelling coefficient of more than 3.0.

Pure enzyme of hydrolytic action is prepared by dissolving the lyophilized powder in a 0.001M solution of calcium chloride and passed through chromatographic columns packed with Sephadex or some other sorbent similar in its sieve effect. This process is repeated three times. The solution purified from the associated ballast substances and salts is lyophilized.

The enzymatic preparation was prepared by concentrating the solution by vacuum-evaporation (at temperatures not above 40° C) of the culture filtrate passed through the ion-exchange columns, which absorb the antibiotic hygromycin B, with subsequent drying of the concentrate on a spraying drier at the inlet air temperature of 110° – 130° C.

The enzymatic preparation can also be prepared from the culture fluid (without separating the biomass) by autolyzing it preliminarily by heating to 40° C for thirty minutes, with subsequent sorption of the antibiotic hygromycin B on a suspended bed of cation-exchange resin, followed by vaccum-evaporation and drying.

The enzyme can be isolated and purified by sorption from the culture filtrate on ion-exchange resins, for example, caboxyl cationite, with subsequent elution of the enzyme from the ion-exchanger by a buffer solution, and drying the said solution.

For a better understanding of the invention, the following examples of its practical embodiment are given by way of illustration.

EXAMPLE 1

50-ml portions of nutrient medium containing 1.5 percent by weight of soya bean flour, 0.2 percent by weight of corn steep liquor, 2 percent by weight of sperm oil, 1 percent by weight of dry yeast (protein-vitamin complex), 0.2 percent by weight of ammonium sulphate, 0.5 percent by weight of sodium chloride, 0.3 percent by weight of calcium carbonate and 1 percent by weight of glucose, are placed into ten flasks of 750-ml capacity. The culture medium is then inoculated with 48-hour-old culture of *Streptomyces hygroscopicus* No. 1913, variant No. 149, taken in an amount of 10 percent by volume. This variant was prepared from the culture *Streptomyces hygroscopicus*, strain No. 1913, by the action of X-rays (200,000 roentgens).

Variant No. 149 well propagates on culture medium No. 21/12 to form convex, sometimes laminar colonies, 6 – 8 mm in dia., the aerial mycelium is developed moderately, greyish-white in colour, weakly sporulating. The substrate mycelium is yellowish brown. This variant of strain No. 1913 does not produce antibiotic hygromycin B during fermentation, and only produces the enzyme of hydrolytic action (tp 22.0 PU/ml).

The duration of the fermentation process is 148 hours. The fermentation temperature, 28° C. As a result, 500 ml of culture fluid having the proteolytic activity of 20 PU/ml are prepared. The culture fluid is passed through a Buchner funnel to prepare 420 ml of culture filtrate, which is then lyophilized. The yield of the enzymatic preparation, having the activity of 500 PU/g, is 16.4 g.

EXAMPLE 2

200 lit of a nutrient medium having the composition as specified in Example 1, are loaded into a fermentation tank of 300-liter capacity. The medium is inoculated by material grown on a medium having the following composition: 1 percent of soya bean flour, 0.2 percent of corn steep liquor, 1 percent of sperm oil, 1 percent of dry yeast (protein-vitamin complex), 0.2 percent of ammonium sulphate, 0.5 percent of sodium chloride, 0.3 percent of calcium carbonate and 1 percent of glucose. The fermentation is carried out for 54 hours at a temperature of 28° C. Then the pressure is raised to 0.3 atm and the contents are aerated with air delivered at a rate of one volume per volume of the medium per minute. In these conditions the medium is processed for 180 hours at the same temperature of 28° C. The process gives 200 liters of culture fluid containing 2420 units per ml of antibiotic hygromycin B and 36 PU/ml of hygrolytin enzyme. One kg of sodium oxalate at pH 7.0 is then added to the culture fluid to precipitate calcium ion, the mixture is stirred for thirty minutes, and then passed through a filter press to separate the biomass and calcium oxalate. The antibiotic hygromycin B is separated from the thus-obtained culture filtrate by passing through a stationary bed of cation-exchange resin (carboxy resin).

To the 200 liters of the culture filtrate passed through the ion-exchanger, added are 25 g of calcium chloride, the components are mixed and evaporated at a temperature of 30° C to 50 liters. To the 50 liters of the concentrate, 1.5 kg of sodium chloride is added under stirring and the mixture is then dried in a spraying drier at a temperature of the inlet air of 110° C. The process gives 5 kg of the enzymatic preparation protohygrolytin, having the activity of 240 PU/g.

EXAMPLE 3

200 liters of culture fluid prepared in conditions similar to those described in Example 2, and containing 2600 units/ml of the antibiotic hygromycin B and 38 PU/ml of the enzyme, are heated at a temperature of 40° C for thirty minutes, after which the mixture is cooled to 10° C, 1 kg of sodium oxalate is added at pH 7.0, and the contents are mixed for thirty minutes. The antibiotic hygromycin B is then sorbed on a suspended bed of carboxyl cation-exchanger, with the result that the enzymatic preparation protohygrolytin is prepared, as described in Example 2. The yield is 5.4 kg of protohygrolytin having the activity of 200 PU/g.

EXAMPLE 4

To 20 liters of culture filtrate, prepared as described in Example 2 and passed through ion-exchange columns, having the pH 6.8 and proteolytic activity of 33 PU/ml, added under stirring are 10 kg of ammonium sulphate. The mixture is allowed to stand overnight in a refrigerator at a temperature of +4° C. The precipitate is then separated on a centrifuge, and dissolved in 1 liter of a 0.001 M solution of calcium chloride.

One liter of cool acetone (0° C) is added to the solution in the cold and the mixture is kept for thirty minutes in a refrigerator. The precipitate is separated on a centrifuge and dissolved in 300 ml of cooled 30 percent acetone. The insoluble residue is separated. Now 3 liters of cool acetone are added to the supernatant liquid, and the precipitate which falls out is separated by centrifuging, washed with acetone and dried in vacuo. The yield is 30 g of crude product having the activity of 7.4 PU/mg and specific activity of 19.5 PU/mg of protein.

The crude product is dissolved in 3.8 liters of a 0.001M solution of calcium chloride, 50 g of activated carbon (washed to pH 8.5) are added, the components are intermixed for 90 minutes, passed through a Buchner funnel with diatomite element, and through a sterilizing filter. The sterile solution is filled in vials in 150 ml portions and dried by lyophilization.

The yield is 18 g of a sterile medicinal preparation having the activity of 8.8 PU/mg and the specific activity of 23.8 PU/mg of protein.

EXAMPLE 5

18 g of lyophilized preparation, obtained as described in Example 4, are dissolved in 80 ml of a 0.001M solution of calcium chloride and passed through two columns packed with Sephadex G-75, each of which has the dia. of 6 cm, and the height of the sephadex bed of 50 cm. The space rate of passage is 140 ml per hour. The active fraction is collected and dried by lyophilization. The yield is 1.8 g of the preparation having the activity of 38 PU/mg and the specific activity of 42 PU/mg of protein.

1.8 g of the thus-obtained preparation is dissolved in 10 ml of a 0.001M solution of calcium chloride and the solution is passed through a column packed with Sephadex DEAEA-50 in tris-buffer. The diameter of the column is 3.5 cm, the height of the bed, 50 cm. The elution is effected with the tris-buffer having the pH 7.0. The separation is carried out at a temperature of +4° C. The active fraction is isolated and dried by lyophilization. The resultant product is 800 mg of the preparation having the activity of 25 PU/mg and the specific activity of 65 PU/mg protein.

800 mg of the thus-obtained preparation are dissolved in 8 ml of a 0.001M solution of calcium chloride and the solution is desalted by passing through a column packed with Sephadex G-15. The diameter of the columns is 2.5 cm and the height of the bed is 42 cm.

The active fraction is collected and dried lyophilically.

The result is 120 mg of the enzyme of hydrolytic action having the activity of 56 PU/mg and the specific activity of 60 PU/mg protein.

EXAMPLE 6

Hides of cattle were washed and soaked in water free of sharpening agents (i.e., weak alkaline or enzyme solutions), were treated in an aqueous solution of protohygrolytin containing not less than 900 PU/liter, for 24 hours at a temperature of 20° – 25° C. After this procedure the hides were dehaired mechanically.

EXAMPLE 7

Hides of cattle were washed and soaked, after which an aqueous solution of protohygrolytin was applied to their faces (55 – 70 PU per square decimeter). The hides were then stacked face to face and allowed to lie for 24 hours.

After this procedure the hides were scoured on a dehairing machine.

EXAMPLE 8

Hides of calf, goat and sheep were washed and soaked in water, then trimmed, and an aqueous solution of the enzymatic preparation was applied to the flesh side (55 – 70 PU per square decimeter). The hides were then stacked face to face, and allowed to lie for 16 – 24 hours or hang suspended in a chamber during the same period. After this treatment hair was removed from the hides.

EXAMPLE 9

Calf skins, given routine processing, are washed in running water in a moving apparatus for 40 – 60 minutes with gradual raising the temperature to 34° C (at the end of washing).

The de-ashing and softening is carried out in the same apparatus. In 10 – 20 minutes after ammonium sulphate has been added, protohygrolytin is added to the de-ashing bath. The de-ashing and softening are carried out with continuous rotation of the apparatus at a temperature of 32° – 34° C.

The specifications of the processes:

1. de-ashing: duration, 15 – 20 minutes; the consumption of ammonium sulphate 1.5 – 2 percent of the skin weight.

2. softening: duration, 10 – 15 minutes; consumption of protohygrolytin, 0.05 – 0.1 percent of the skin weight (the activity of the preparation being 80 PU).

We claim:

1. A composition having hydrolytic, proteolytic and thrombolytic properties consisting essentially of an effective amount of hygrolytin and a pharmaceutically acceptable carrier, said hygrolytin being the product of the process which comprises cultivating, under deep aerobic conditions, *Streptomyces hygroscopicus*, strain 1913 (All-Union Research Institute of Antibiotics, Moscow, Culture Collection, Deposit No. 997), using an aqueous nutrient medium containing assimilable sources of carbon, nitrogen and inorganic substances, and separating hygrolytin formed during the culture.

2. The composition of claim 1, wherein the concentration of the hygrolytin is from 1 to 50 PU/mg.

3. The composition of claim 1, wherein the active principle is used in combination with a pharmaceutical solvent selected from the group consisting of sterile water for injections, a sodium chloride isotonic solution, a sodium chloride hypertonic solution, and a 0.25 to 2% solution of novocain.

4. The composition of claim 3, wherein the concentration of the active principle is in the range of 5 to 50 PU/ml.

5. The composition of claim 1, wherein the active principle is used in combination with a powdered filler for topical application, the filler being starch.

6. The composition of claim 5, wherein the concentration of the active principle is up to 500 PU per gram of filler.

* * * * *